United States Patent
Kuramori et al.

(10) Patent No.: US 7,421,293 B2
(45) Date of Patent: Sep. 2, 2008

(54) STRESS-AT-WORK JUDGING APPARATUS, STRESS-AT-WORK JUDGING PROGRAM, AND STRESS-AT-WORK JUDGING METHOD

(75) Inventors: Akira Kuramori, Kanagawa (JP); Noritaka Koguchi, Kanagawa (JP); Masayoshi Kamijo, Nagano (JP); Tsugutake Sadoyama, Ibaraki (JP); Satoshi Hosoya, Nagano (JP); Yoshjo Shimizu, Nagano (JP)

(73) Assignee: The Yokohama Rubber Co., Ltd., Tokyo (JP)

(*) Notice: Subject to any disclaimer, the term of this patent is extended or adjusted under 35 U.S.C. 154(b) by 427 days.

(21) Appl. No.: 10/522,022

(22) PCT Filed: Jul. 18, 2003

(86) PCT No.: PCT/JP03/09160

§ 371 (c)(1), (2), (4) Date: Jan. 21, 2005

(87) PCT Pub. No.: WO2004/008958

PCT Pub. Date: Jan. 29, 2004

(65) Prior Publication Data
US 2005/0245838 A1 Nov. 3, 2005

(30) Foreign Application Priority Data
Jul. 22, 2002 (JP) ............................... 2002-212683

(51) Int. Cl.
*A61B 5/04* (2006.01)
*A61B 5/103* (2006.01)
*G08B 23/00* (2006.01)
*B60K 28/00* (2006.01)

(52) U.S. Cl. ........................ 600/546; 600/590; 340/576; 180/272

(58) Field of Classification Search ................. 600/546, 600/590; 340/576; 73/379.01, 379.02
See application file for complete search history.

(56) References Cited

U.S. PATENT DOCUMENTS

| 4,344,441 A | 8/1982 | Radke |
| 4,934,378 A | 6/1990 | Perry |
| 5,195,531 A * | 3/1993 | Bennett ....................... 600/546 |
| 6,233,472 B1 * | 5/2001 | Bennett et al. ................ 600/546 |

FOREIGN PATENT DOCUMENTS

| JP | 57-043730 | A1 | 3/1982 |
| JP | 2002-214083 | A1 | 7/2002 |
| JP | 2002230699 | A * | 8/2002 |
| JP | 2003-177079 | A1 | 6/2003 |

OTHER PUBLICATIONS

Healey, Jennifer A. "Wearable and automotive systems for affect recognition from physiology." May 2000. Massachusetts Institute of Technology. All, particularly pp. 93-126.*

(Continued)

*Primary Examiner*—Max Hindenburg
*Assistant Examiner*—John Pani
(74) *Attorney, Agent, or Firm*—Knobbe Martens Olson & Bear LLP (57) ABSTRACT

A stress-at-work judging apparatus, program, and method for judging the stress exerted on the subject at work such as steering of a vehicle by the subject. An myoelectric potential signal of the masseter muscle is inputted during an object work carried out by the activity of muscles independent of the activity of the masseter muscle opening/closing the jaw of the subject. The myoelectric potential signal representing a change of the activity of the masseter muscle and generated when the object work acts as a stressor of the subject is used to judge the stress. A camera or microphone is disposed near the subject to exclude the period during which the subject speaks or masticate by using the masseter muscle independently of the object work from the object period during which stress is judged.

9 Claims, 4 Drawing Sheets

OTHER PUBLICATIONS

Okamoto et al. "Driving load decision device, driving load decision method, computer program for implementing said method, and storage medium in which said computer program is stored." English translation of JP2002-230699.*

Manabu Yoshikawa et al., "Sokoji ni Okeru Untensha no Shinshin Han'no no Keisoku", Dai 11 Kai Shinshu Chiku Keisoku Seigyo Kenkyu Koenkai Koen Ronbunshu, Keisoku Jido Seigyo Gakkai Chubu Shibu Shinshu Chiku Keisoku Seigyo Kenkyu Iinkai, 1998, pp. 1-4.

International Search Report for PCT/JP03/09160 mailed on Sep. 2, 2003.

Okamoto, Nobuhisa, et al. "Driving load decision device, driving load decision method, computer program for implementing said method, and storage medium in which said computer program is stored." English translation of JP-2002230699 by Schreiber Translations, Inc. May 2007.

Lehman, Gregory, et al. "The importance of normalization in the interpretation of surface electromyography. A proof of principle." Sep. 1999. Journal of Manipulative and Physiological Therapeutics. vol. 22, No. 7, pp. 444-446.

Office Action dated Jul. 30, 2007 from co-pending U.S. Appl. No. 10/522,023, filed Jan. 21, 2005.

Nicholson, R.A. et al. "Influence of a scheduled -waiting task on EMG reactivity and oral habits among facial pain patients and no-pain controls," Applied Psychophysiology and Biofeedback. Dec. 2000 (pp. 203-219), vol. 25, No. 4.

Ruf, Sabine et al., "Stress-induced changes in the functional electromyographic activity of the masticatory muscles," Database Biosis [Online] Biosciences Information Service, 1997, Database accession No. PREV19979458422; and ACTA Odontologica Scandinavica (pp. 44-48), vol. 55, No. 1, 1997.

Dahlstrom, L. et al. "Stress-induced muscular activity in mandibular dysfunction effects of biofeedback training," Database Biosis [Online] Biosciences Information Service, 1985, Database accession No. PREV198580099428; and Journal of Behavioral Medicine (pp. 191-200), vol. 8, No. 2, 1985.

Moss, R.A. et al. "Physiological reactions to stress in subjects with and without myofascial pain dysfunction symptoms," Database Biosis [Online] Biosciences Information Service, 1984, Database accession No. PREV198580007800; and Journal of Oral Rehabilitation (pp. 219-232), vol. 11, No. 3, 1984.

Supplemental European Search Report, dated May 27, 2008.

* cited by examiner

STRESS-AT-WORK JUDGING APPARATUS, STRESS-AT-WORK JUDGING PROGRAM, AND STRESS-AT-WORK JUDGING METHOD

TECHNICAL FIELD

The present invention relates to a stress-at-work judging apparatus, a stress-at-work judging program, and a stress-at-work judging method and, more particularly, to a judging apparatus for judging stress exerted on a test subject by an activity on which he or she is working.

BACKGROUND ART

A method using biological information, such as an electrocardiogram or brain wave, is known for a general technique for measuring a mental burden (stress) of a subject. The method using biological information requires regulated conditions to a test subject in many cases and needs a relatively long time to analyze the data. For this reason, the method is used for judging stress of a subject in a resting condition.

A person frequently suffers from large stress when he/she drives a vehicle etc. (stress at work). A situation where the person suffers from the stress and a level of the stress vary from person to person. For example, in a situation where vehicle ride is uncomfortable or steering performance is poor, excessive strain is apt to occur in the person. Such excess strain is likely to hinder a smooth driving, possibly causing an accident.

In development and design for a vehicle etc., an electromyogram, which is easily measured and high in responsivity among biological information, is obtained from myoelectric potential signals indicating activities of the muscles of parts of the human body whose loads are large during driving, such as the arms and the feet, and a burden of the test subject at driving is directly judged.

Generally, when a human being suffers from a mental burden from stress, "strain" as unintentional excessive muscle activity generally appears. Accordingly, such a mental stress can be measured by measuring an activity state of the muscle.

Muscle activities of the arms and the feet, which are largely engaged in work such as driving of a vehicle, are measured in the form of an electromyogram, movement of the muscles at work is measured, and a physical burden of a human body is judged in conventional cases. However, a mental burden (stress) at work cannot be objectively expressed on the basis of this electromyogram.

For example, in the electromyogram describing the activities of the muscles at work such as the arm and the foot, a myoelectric potential signal representing the muscle activities by work such as driving of a vehicle and a myoelectric potential signal representing the muscle "excessive strain" due to the stress are superposed on each other. It is thus difficult to discriminate the muscle activity by the stress from the muscle activity of driving.

The method using biological information other than the electromyogram often requires regulations of a test subject and needs a relatively long recording time to analyze the data. Therefore, it is difficult to correctly evaluate stress at work.

In conventional development and design for a vehicle etc., items relating to the mental burden (stress), such as riding comfort and steering performance, are merely described in terms of a test subject feeling that is subjectively judged in words. As a result, it is impossible to objectively judge the stress.

The present invention has been made in view of the above, and has an object to provide a stress-at-work judging apparatus which can objectively judge stress at work by quantitatively measuring the "strain" that is generated from stress at work such as driving of a vehicle, a stress-at-work judging program and a stress-at-work judging method.

DISCLOSURE OF THE INVENTION

According to the present invention, to achieve the above object, a stress-at-work judging apparatus including: myoelectric potential signal input means for receiving a myoelectric potential signal from a masseter muscle of a test subject during a target work activity performed through a movement of a muscle independent of a movement of the masseter muscle which is opening and closing jaws of the test subject; and stress judging means for judging stress from the myoelectric potential signal showing a change in the movement of the masseter muscle which appears when the target work activity acts as a stressor on the test subject.

Since the constitution allows the judgment of the stress undergone by the test subject through the recognition of a change in an at-work myoelectric potential signal while he or she is working on the activity, it becomes possible to quantitatively represent an item appearing as a mental burden on the test subject while he or she is steering a wheel as a driver (during a work activity), such as, e.g., vehicle ride comfort or steering performance, and objectively judge the stress during the steering of the wheel (during the work activity).

When stress is placed on the test subject, "strain" develops in his or her muscle. If the degree of the "strain" is measured at this time, the stress can be judged. However, since various muscles are moving in response to a work activity, it is assumed that, to precisely measure the "strain", a muscle which is conceivably not used mainly during the work activity may be measured appropriately. In particular, a strong force is exerted on the jaws as a result of teeth clenching when stress develops so that, in the case where the test subject is working on an activity which mainly uses muscles in such parts as arms and legs, the judgment of the stress is enabled by measuring the movement of masseter muscles in the jaws of the test subject and thereby recognizing the intensity of the movement and the time-varying change thereof.

It is to be noted that target work activities indicate any work activities except for a work activity which positively uses jaws, such as work activities using hands, legs, fingers, a waist, hips, and a back. A specific test subject is, e.g., an operator of an automobile, a motorcycle, a ship, an aircraft, or the like, a plant operator in a factory, an OA (office automation) operator, a clerical worker, or the like. The movement of a muscle independent of the movement of the masseter muscles of a test subject which is opening and closing his or her jaws means any muscle movement except for an action which positively uses the jaws such as speaking, yawning, or chewing. A stressor is a stimulus which causes stress.

The stress-at-work judging apparatus is characterized in that the stress judging means excludes a period during which the test subject performs a predetermined work activity which uses the masseter muscle independently of the target work activity from a target period for stress judgment.

With the constitution, even when the test subject performs a predetermined work activity using his or her masseter muscles independently of the target work activity while he or she is engaged in the target work activity, if there is a change in muscle movement resulting from the predetermined work activity using the masseter muscles independently of the target work activity, it is judged that the test subject is engaged in the predetermined work activity using his or her masseter muscles independently of the target work activity and a myoelectric potential signal acquired at that time is not used. This enables precise judgment of the stress.

For example, when stress is judged by obtaining an electromyogram of the masseter muscle of the test subject while he or she is driving a car, if the test subject performs the action of speaking by using the masseter muscles, the masseter muscles are activated by the behavior of speaking so that it appears on the electromyogram distinctly different from "strain" resulting from the stress. In this case, the stress can be judged precisely by judging that the test subject is engaged in the predetermined work activity using the masseter muscles independently of the target work activity while he or she is performing the speaking action and not using the obtained electromyogram for the judgment of the stress.

Further, in the stress-at-work judging apparatus, the stress judging means specifies the period during which the test subject performs the predetermined work activity which uses the masseter muscle independently of the target work activity from voice data acquired by inputting a speech of the test subject or from image data acquired by inputting an image of a face of the test subject.

With this constitution, it is possible to specify a period during which the test subject performs a predetermined work activity which uses the masseter muscle independently of the target work activity.

Note that, in the stress-at-work judging apparatus according to the present invention, the target work is preferably a vehicle steering operation performed by the test subject.

As a parameter used for the stress judgment, the intensity of a myoelectric potential signal can be listed, examples of which include a root mean square (RMS) and an integral value (IEMG (Integrated Electromyogram)) measured in a given time. Such parameters may be calculated appropriately by using various calculating means. It is appropriate for the calculating means to preliminarily define functions for calculating the RMS and IEMG and perform calculation processes with respect to inputted myoelectric potential signals in time-series order.

The intensity of a myoelectric potential signal such as the RMS or IEMG is calculated, e.g., every time a given action is performed. For example, when a driver has been driving a car over a plurality of sections, it becomes possible to calculate the intensity of the myoelectric potential signal for each of the sections and observe the tendency in each of the sections. The intensity of the myoelectric potential signal may be calculated appropriately by, e.g., intensity calculating means.

Preferably, means for recognizing a predetermined work activity using the masseter muscles independently of the target work activity recognizes an action during which the masseter muscles primarily function, such as chewing or speaking, which is the predetermined work activity performed by the test subject during the target work activity by using the masseter muscles independently of the target work activity. In this case, it is appropriate for the stress judging means to judge that a change in the at-work myoelectric potential signal is due to the predetermined work activity using the masseter muscles independently of the target work activity, such as chewing or speaking.

Further, to attain the above-mentioned object, an at-work judging program according to the present invention includes each means of the stress-at-work judging apparatus as a program module executed by a computer.

That is, the present invention provides a computer-executable program for causing a computer to perform stress-at-work judgment, the computer-executable program including: an input procedure for causing calculating means of the computer to receive a myoelectric potential signal from a masseter muscle of a test subject during a target work activity performed through a movement of a muscle independent of a movement of the masseter muscle which is opening and closing jaws of the test subject; and a judgment procedure for causing the calculating means of the computer to judge stress from the myoelectric potential signal showing a change in the movement of the masseter muscle which appears when the target work activity acts as a stressor on the test subject.

At that time, the computer-executable program is characterized in that the stress judging judgment procedure causes the calculation means to exclude a period during which the test subject performs a predetermined work activity which uses the masseter muscle independently of the target work activity from a target period for stress judgment. Further, in this case, the stress judging judgment procedure causes the calculation means to specify the period during which the test subject performs the predetermined work activity which uses the masseter muscle independently of the target work activity from voice data acquired by inputting a speech of the test subject or from image data acquired by inputting an image of a face of the test subject.

Further, a vehicle steering operation performed by the test subject is exemplified as the target work, for example.

Note that, the above-mentioned program may not only be a program constructed by dividing individual means for implementing respective procedures into module units but also be one program including the individual procedures. The present invention also includes this case. This is because, even though the individual procedures are incorporated in one program, the individual procedures are incorporated in the modules units on the computer so that they are substantially modulized.

Moreover, to achieve the above object, the present invention provides a stress-at-work judging method including: a myoelectric potential signal input step of receiving a myoelectric potential signal from a masseter muscle of a test subject during a target work activity performed through a movement of a muscle independent of a movement of the masseter muscle which is opening and closing jaws of the test subject; and a stress judging step of judging stress from the myoelectric potential signal showing a change in the movement of the masseter muscle which appears when the target work activity acts as a stressor on the test subject.

Since the constitution allows the judgment of the stress undergone by the test subject through the recognition of a change in the at-work myoelectric potential signal while he or she is working on the activity, it becomes possible to quantitatively represent an item appearing as a mental burden such as, e.g., vehicle ride comfort or steering performance and objectively judge stress during the work activity.

Further, in this case, the stress-at-work judging method is characterized in that the stress judging step includes excluding a period during which the test subject performs a predetermined work activity which uses the masseter muscle independently of the target work activity from a target period for stress judgment. At that time, the period during which the test subject performs the predetermined work activity which uses the masseter muscle independently of the target work activity is specified from voice data acquired by inputting a speech of the test subject or from image data acquired by inputting an image of a face of the test subject, for example.

Furthermore, the target work is, for example, a steering operation performed by the test subject.

BEST MODE FOR CARRYING OUT THE INVENTION

A detailed description will be given below to a stress-at-work judging apparatus, a stress-at-work judging program, and a stress-at-work judging method according to the present invention based on a preferred embodiment shown in the accompanying drawings. The present invention is by no means restricted by the embodiment. The description will be given below to the case where a test subject is engaged in a work activity which uses muscles in arms, legs, and the like, such as the driving of a car.

Figure 1:
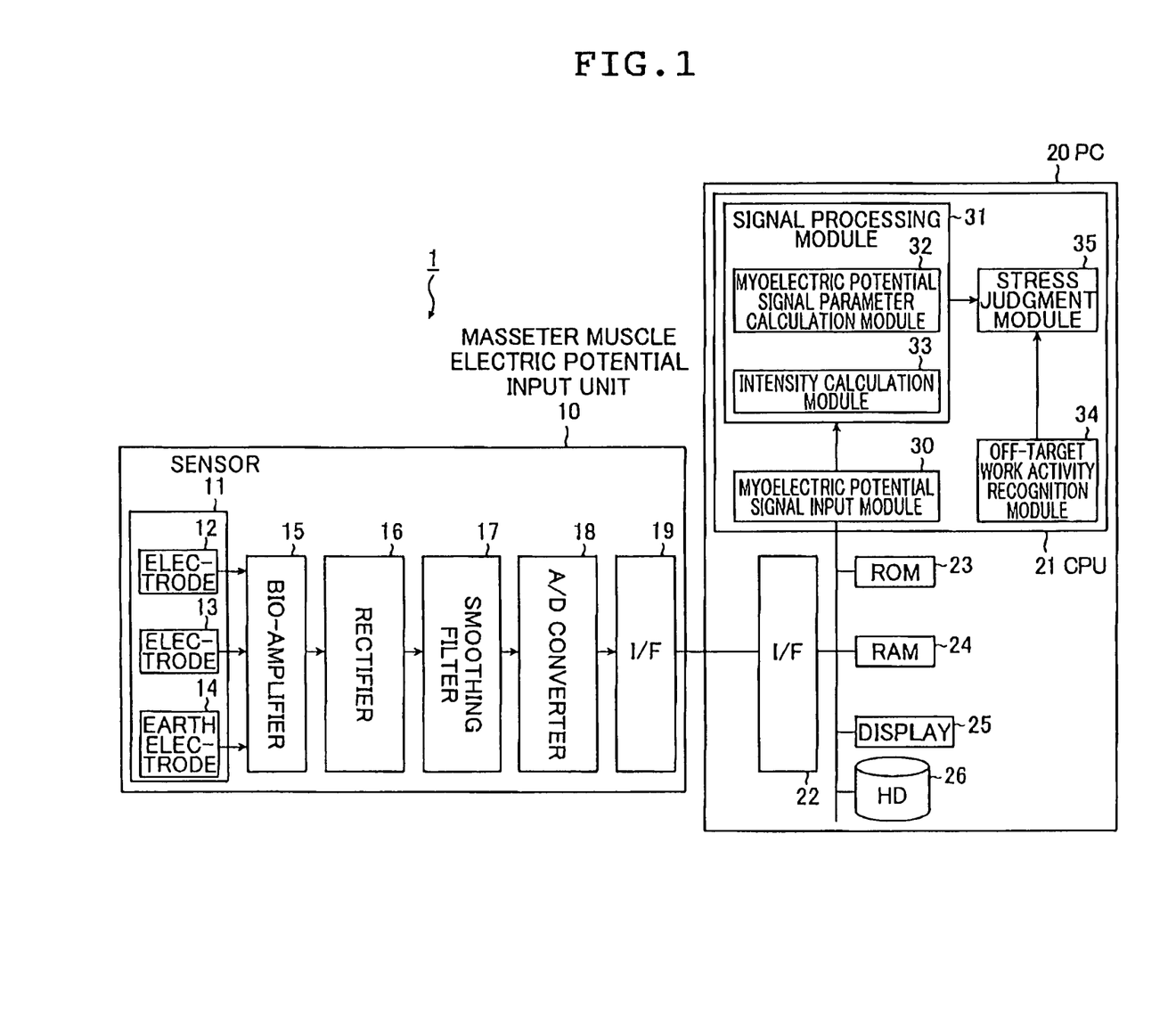
FIG. 1 is a block diagram illustrating a structure of a stress-at-work judging apparatus according to an embodiment of the present invention.
Figure 2:
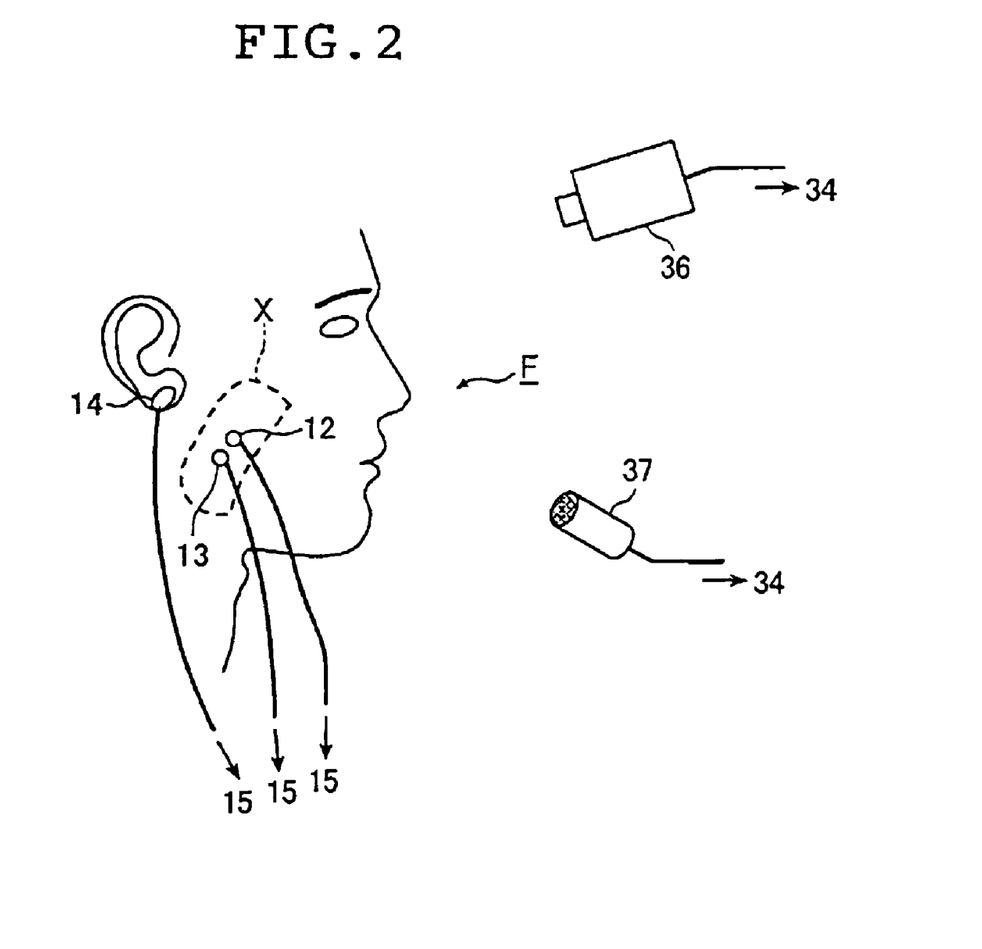
FIG. 2 is a view showing an example of the mounting of electrodes to which myoelectric potential signals for sensing stress during a work activity are inputted according to the embodiment of the present invention.

FIG. 1 is a block diagram illustrating a structure of the stress-at-work judging apparatus according to the embodiment of the present invention. FIG. 2 is a view showing an example of the mounting of electrodes to which myoelectric potential signals for sensing stress during a work activity are inputted according to the embodiment of the present invention.

In FIG. 1, a stress-at-work judging system 1 is composed of a masseter muscle electric potential input unit 10 to which the action electric potential of a masseter muscle is inputted and a personal computer (PC) 20 for judging stress based on the myoelectric potential signal inputted to the masseter muscle potential input unit 10.

The masseter muscle electric potential input unit 10 senses the action potential of the masseter muscle by using a sensor 11. The sensor 11 is constituted by electrodes 12 and 13 disposed in spaced apart relation at a distance of about 5 mm and an earth electrode 14 placed at a reference potential. As shown in FIG. 2, the electrodes 12 and 13 are attached to the skin of the upper portion of a masseter muscle X (the broken line) of a face F, while the earth electrode 14 is attached to an earlobe.

Here, the masseter muscle is a large muscle present on either side of the face and called a chewing muscle together with a temporal muscle. The masseter muscle acts on the actions of closing jaws, e.g., chewing and speaking actions. Accordingly, the masseter muscle does not normally move during a work activity such as the driving of a car performed by using muscles in arms, legs, and the like. If stress develops in a test subject and causes him or her to tense all over, however, "strain" also develops in the masseter muscle. In this embodiment, a myoelectric potential signal from the masseter muscle is measured when the stress has developed.

Referring again to FIG. 1, the masseter muscle electric potential input unit 10 has: a bio-amplifier 15 which amplifies a myoelectric potential signal from the sensor 11; a rectifier 16 which rectifies the myoelectric potential signal having an ac waveform to a myoelectric potential signal having a dc waveform; a smoothing filter 17 which removes noise in the myoelectric potential signal therefrom; an A/D converter 18 which converts the myoelectric potential signal as an analog signal to a digital signal; and an interface (I/F) 19 which controls the exchange of data with the PC 20.

In the masseter muscle electric potential input unit 10, when the test subject undergoes stress due to right turn or left turn during the driving of a car (during a work activity) and tenses up all over so that "strain" develops in the masseter muscle, the myoelectric potential signal composed of the analog waveform of a myoelectric potential signal resulting from the "strain" developed at that time is inputted from the electrodes 12 and 13, amplified by the bio-amplifier 15, rectified by the rectifier 16, further subjected to noise removal by the smoothing filter 17, converted to a digital signal by the A/D converter 18, and transferred to the PC 20 through the I/F 19.

On the other hand, the PC 20 is a stress-at-work judging apparatus which judges stress during the work activity based on the myoelectric potential signal transferred from the masseter muscle potential input unit 10 and primarily has: a CPU 21 which invokes various program modules as required and administers an overall process; an interface (I/F) 22 which controls the exchange of data between the masseter muscle electric potential input unit 10 and the PC 20; a ROM 23 and a RAM 24 which store therein various programs executed by the CPU 21 and various data items; a display 25 which displays a result of stress judgment and the like; and a hard disk (HD) 26 which stores therein the myoelectric potential signal transferred from the masseter muscle electric potential input unit 10, the various programs, and the various data items. The CPU 21, the I/F 22, the ROM 23, the RAM 24, the display 25, and the HD 26 are connected to each other via buses.

Here, each of the programs has an input procedure which causes calculating means of the computer to receive a myoelectric potential signal from the masseter muscle during the target work activity performed through the movement of a muscle independent of the movement of the masseter muscles which open and close the jaws of the test subject and a judgment procedure which causes the calculating means of the computer to judge the stress from the myoelectric potential signal showing a change in the movement of the masseter appearing when the target work activity acts as a stressor on the test subject.

Then, the CPU 21 executes a stress judging process by particularly invoking: a myoelectric potential signal input module 30 which receives a myoelectric potential signal from the masseter muscle during the target work activity performed through the movement of a muscle independent of the movement of the masseter muscles which open and close the jaws of the test subject; a signal processing module 31 which processes the myoelectric potential signal to a parameter as an index for stress judgment (e.g., a myoelectric potential signal parameter calculation module 32 which calculates a myoelectric potential signal parameter based on a function of a root mean square (RMS) or an integral value (IEMG) (Integrated Electromyogram) measured in a given time or an intensity calculation module 33 which calculates a parameter based on the intensity of the myoelectric potential signal); an off-target work activity recognition module 34 which recognizes a predetermined work activity performed by the test subject by using the masseter muscles independently of the target work activity during the target work activity; and a stress judgment module 35 which judges the stress by recognizing a change in the movement of the muscle appearing when the target work activity acts as a stressor on the test subject from a change in the at-work myoelectric potential signal.

Each of these modules may be stored in any of the ROM 23, the RAM 24, and the HD 26. The individual modules may be stored separately from each other. The modules may also be stored in a CD-ROM or another storage medium not shown in the drawings.

The myoelectric potential signal input module 30 is means for receiving an at-work myoelectric potential signal from the masseter muscle during the target work activity performed through the movement of a muscle independent of the movement of the masseter muscles which open and close the jaws of the test subject. For example, the myoelectric potential signal input module 30 receives, when a work activity for stress judgment is the driving of a car, a myoelectric potential signal from the masseter muscle of the test subject during the driving of a car (during a work activity). When the test subject particularly feels stress, the stress appears as "strain" in the masseter muscle. The myoelectric potential signal when the "strain" has developed has a potential higher than that of a myoelectric potential signal in the absence of the "strain" when the test subject feels no stress.

Note that, the myoelectric potential signal input module 30 may not only receive the myoelectric potential signal transferred in real time from the masseter muscle electric potential input unit 10 but also accumulate the myoelectric potential signal transferred from the masseter muscle potential input unit 10 in the HD 26 and read the accumulated myoelectric potential signal from the HD 26.

The signal processing module 31 mentioned above is means for processing the myoelectric potential signal to a parameter as an index for the judgment by the stress judgment module 35. The signal processing module 31 is composed of: the myoelectric potential signal parameter calculation module 32 which preliminarily defines a function for calculating, e.g., the RMS or IEMG and performs a calculation process with respect to the inputted myoelectric potential signal in time-series order; and the intensity calculation module 33 which calculates a parameter based on the intensity of the myoelectric potential signal.

The myoelectric potential signal parameter calculation module 32 mentioned above obtains, e.g., an integral value of a change in the myoelectric potential signal from the masseter muscle which is transferred from the masseter muscle potential input unit 10 and gives, when a sharp change occurs, the obtained value to the stress judgment module 35 to show that stress has resulted from an action.

Then, the intensity calculation module 33 obtains, e.g., a value such as a peak value or mean value of the intensities of myoelectric potential signals, such as the RMS, IEM, or the like, which are measured every time a given action is performed, compares the intensities of the myoelectric potential signals measured every time the given action is performed, and gives the result of comparison to the stress judgment module 35. The judgment of the intensities may also be performed by using the IEMG or RMS normalized to a maximum myoelectric potential that has been measured preliminarily and based on a threshold value prepared in advance.

The off-target work activity recognition module 34 is means for recognizing a predetermined work activity performed by the test subject during a target work activity by using the masseter muscles independently of the target work activity and giving the result of recognition to the stress judgment module 35. The off-target work activity recognition module 34 is also constituted to function as means for recognizing an action during which the masseter muscles primarily function, such as chewing or speaking, which is the predetermined work activity performed by the test subject during the target work activity by using the masseter muscles independently of the target work activity and giving the result of recognition to the stress judgment module 35.

Alternatively, the off-target work activity recognition module 34 may also be constituted to function as means for recognizing the action of the predetermined work activity using the masseter muscles independently of the target work activity from video data acquired by shooting the predetermined operation using, during the target work actively, the masseter muscles independently of the target work actively and giving the result of recognition to the above-mentioned stress judgment module 35. In this case, a camera 36 is placed to face the test subject, video image date from the camera 36 is fetched by the PC 20, and the off-target work actively recognition module 34 visually recognizes the chewing or speaking condition from the fetched image data and recognizes the condition of either of chewing and speaking actions. In this case, either the chewing action or the speaking action can be recognized as a predetermined work actively using the masseter muscles independently of the target work actively.

Alternatively, the off-target work activity recognition module 34 may also recognize speaking as the action of the predetermined work activity using the masseter muscles independently of the target work activity from voice data acquired by recording a speech and give the result of recognition to the stress judgment module 35. In this case, it is necessary to place a microphone 37 shown in FIG. 2 in the vicinity of the test subject such that the voice data from the microphone 37 is fetched by the PC 20. In this case, it is recognized that the test subject is speaking.

The stress judgment module 35 is means for judging stress by recognizing a change in the movement of a muscle appearing when the target work activity acts as a stressor on the test subject from a change in the at-work myoelectric potential signal.

In this case, the stress judgment module 35 allows the judgment of stress undergone by the test subject through the recognition of the stress during the work activity from a change in the at-work myoelectric potential signal by using the myoelectric potential signal input module 30 while he or she is working on an activity. As a result, it becomes possible to quantitatively represent an item appearing as a mental burden such as, e.g., vehicle ride comfort or steering performance, and objectively judge the stress during the work activity.

The stress judgment module 35 is also means for making a judgment based on at least one of the magnitude of a myoelectric potential signal recognized from the above-mentioned myoelectric potential signal and the intensity thereof recognized from the intensity of the myoelectric potential signal.

When the myoelectric potential signal parameter calculation module 32 obtains, e.g., a differential value of a change in the myoelectric potential signal from the masseter muscles that has been transferred from the masseter muscle electric potential input unit 10 and gives the obtained value to the stress judgment module 35 in the event or the occurrence of a sharp change, the stress judgment module 35 judges that stress has occurred in the myoelectric potential signal.

Further, when the intensity calculation module 33 obtains, e.g., a value such as a peak value or mean value of the intensities (RMS, IEMG, or the like) of myoelectric potential signals measured every time a given action is performed, compares the intensities of the myoelectric potential signals measured every time the given action is performed, and gives the result of comparison to the stress judgment module 35, the stress judgment module 35 judges variations and intensities from the result of comparison and specifies an action which has caused the stress.

Thus, according to the stress judgment module 35, it can be judged that, if the magnitude of each of the myoelectric potential signals before and after the work activity is small and the magnitude of the myoelectric potential signal during the work activity is large, the test subject has undergone stress during the work activity from the magnitude change and that, if the intensity of each of the myoelectric potential signals before and after the work activity is low and the intensity of the myoelectric potential signal during the work activity is high, the test subject has undergone stress during the work activity from the intensity change. The stress can also be represented quantitatively as the magnitude or intensity of the myoelectric potential signal resulting from "strain" in a muscle.

The stress judgment module 35 also functions as means for judging, when the predetermined work activity using the masseter muscles independently of the above-mentioned target work activity is an action using a muscle from which the at-work myoelectric potential signal is received, that a change in the at-work myoelectric potential signal mentioned above is due to the predetermined work activity using the masseter muscles independently of the target work activity. For example, when the off-target work activity recognition module 34 recognizes the predetermined work activity using the masseter muscles independently of the target work activity as an action during which the masseter muscles primarily function, such as chewing or speaking, the stress judgment module 35 judges that the change in the at-work myoelectric potential signal mentioned above is due to the predetermined work activity using the masseter muscles independently of the target work activity, such as chewing or speaking.

In this case, regarding the stress judgment module 35, even though the test subject has performed the predetermined work activity using the masseter muscles independently of the target work activity while he or she is engaged in the target work activity, if there is a change in the movement of a muscle due to the predetermined work activity using the masseter muscles independently of the target work activity, the off-target work activity recognition module 34 recognizes that the change was due to the predetermined work activity using the masseter muscles independently of the target work activity and the stress judgment module 35 judges that the test subject is engaged in the predetermined work activity using the masseter muscles independently of the target work activity without using the at-work myoelectric potential signal obtained at that time for stress judgment. This allows the stress judgment module 35 to discern an electromyographic change due to the predetermined work activity using the masseter muscles independently of the target work activity and precisely judge the stress.

For example, when stress is judged by obtaining an electromyogram of the masseter of a test subject while he or she is driving a car, if the test subject speaks, the stress judgment module 35 judges that the test subject is engaged in the predetermined work activity using the masseter muscles independently of the target work activity by attributing the movement of the masseter muscles of the test subject to the speech and does not use the result of recognition for stress judgment, so that stress is judged precisely.

A description will be given below to a judging process in the stress-at-work judging system 1 described above by mainly referring to the operation of the PC 20. Note that, as described above, the electrodes 12 and 13 and the earth electrode 14 are attached preliminarily to the skin of the upper portion of the masseter muscle or earlobe of the test subject. It is assumed that, in this condition, a masseteric myoelectric potential signal is transmitted from each of the electrodes 12 and 13 to the PC 20 via the bio-amplifier 15, the rectifier 16, the smoothing filter 17, the A/D converter 18, and the I/F 19.

Figure 3:
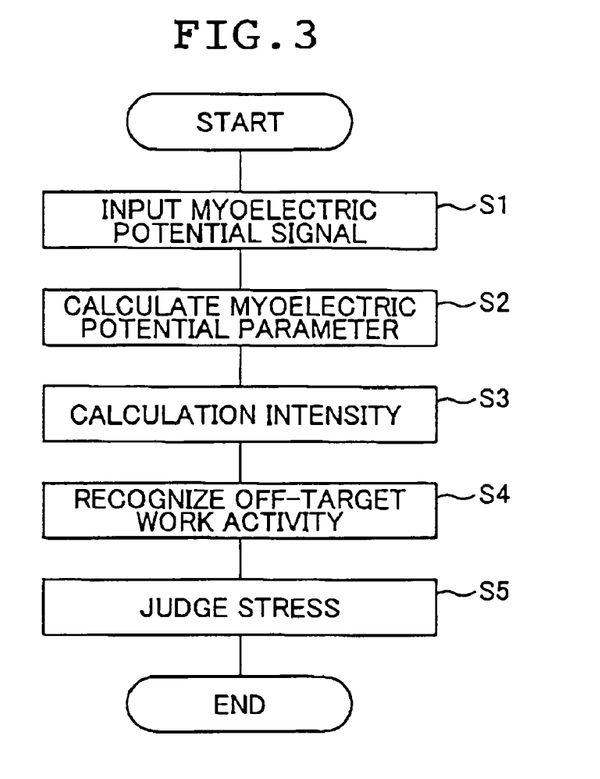
FIG. 3 is a flow chart illustrating a stress-at-work judging process according to the embodiment of the present invention.

FIG. 3 shows a flow chart which illustrates the stress-at-work judging process according to the embodiment of the present invention. In the CPU 21, the myoelectric potential signal input module 30 receives the myoelectric potential signal and gives it to the signal processing module 31 (S1). In the signal processing module, the myoelectric potential signal parameter calculation module 32 obtains, e.g., a differential value of a change in the masseteric myoelectric potential signal transferred from the masseter muscle electric potential input unit 10 and gives, when a sharp change occurs, the obtained value to the stress judgment module 35 to show that stress has developed as a result of an action, as described above (S2). The intensity calculation module 33 obtains, e.g., a value such as a peak value or mean value of the intensities of the myoelectric potential signals measured every time a given action is performed, compares the intensities of the myoelectric potential signals measured every time the given action is performed, and gives the result of comparison to the stress judgment module 35, as described above (S3). At this stage, the off-target work activity recognition module 34 judges the presence or absence of a predetermined work activity using the masseter muscles independently of the target work activity, recognizes the predetermined work activity performed by the test subject during the target work activity by using the masseter muscles independently of the target work activity, and gives the result of recognition to the stress judgment module 35 (S4).

Upon receipt of the result, the stress judgment module 35 recognizes a change in the movement of a muscle appearing when the target work activity acts as a stressor on the test subject from a change in the at-work myoelectric potential signal and judges stress (S5). When the myoelectric potential signal parameter calculation module 32 obtains, e.g., a differential value of a change in the masseteric myoelectric potential signal transferred from the masseter muscle electric potential input unit 10 and gives, when a sharper change occurs compared to the set change, the obtained value to the stress judgment module 35, the stress judgment module 35 judges that stress has occurred in the myoelectric potential signal. When the above-mentioned intensity calculation module 33 obtains, e.g., a value such as a peak value or mean value of the intensities (RMS, IEMG, or the like) of the myoelectric potential signals measured every time a given action is performed, compares the intensities of the myoelectric potential signals measured every time the given action is performed, and gives the result of comparison to the stress judgment module 35, the stress judgment nodule 35 judges variations and intensities from the result of comparison and specifies an action that has caused the stress. When the predetermined work activity using the masseter muscles independently of the target work activity is recognized in S4 described above, the stress judgment module 35 judges that the test subject is engaged in the predetermined work activity using the masseter muscles independently of the target work activity.

According to the embodiment described above, it becomes possible to sense stress during a work activity such as the driving of a car as the movement of a muscle appearing as strain to judge the stress and thereby objectively judge the stress during the work activity. In particular, the embodiment described above allows the measurement of a myoelectric potential signal from the masseter and the judgment of stress from "strain" resulting from teeth clenching based on the result of measurement. In addition, the embodiment described above has used an electromyogram for the judgment. This reduces restrictions on a test subject compared with the case where another bio-information such as electroencephalogram or electrocardiogram is used and allows the recognition of the psychological condition of the test subject from the result of extremely short-period measurement so that evaluation is performed with higher precision.

Thus, according to this embodiment, it becomes possible to recognize stress undergone by a test subject while he or she is working on an activity from a change in a myoelectric potential signal during the work activity and judge the stress during the work activity. This allows the quantitative representation of an item appearing as a mental burden such as, e.g., vehicle ride comfort or steering performance and the objective judgment of the stress during the steering of a wheel (during a work activity).

Although the above-mentioned embodiment has described the case where the movement of the masseter is a measurement target, it is not limited to the masseter provided that a muscle other than the muscle which mainly moves during the work activity is a measurement target. In the case where stress during speech is judged, e.g., the action electric potential of a muscle in an arm or a leg which is not directly relevant to the speech may also be measured appropriately.

Although each of the means including the stress judging means has been described as a module composing a program which is executed by the CPU in the above-mentioned embodiment, it is not limited thereto. Each of the means may also be constructed appropriately as an electronic circuit on an LSI chip or the like.

Although the above-mentioned embodiment has described the case where the rectifier 16 is provided in the masseter muscle potential input unit 10 mentioned above and a myoelectric potential signal is processed to a dc component, the myoelectric potential signal may also be processed appropriately as an ac component without conversion. In this case, the bio-amplifier 15 and the smoothing filter 17 are connected directly to each other.

EXAMPLE

An example of stress evaluation obtained by the stress judging process according to the embodiment described above will be shown below. In the case shown herein, a work activity is the steering of a vehicle wheel. A plurality of work activities show work activities under different running conditions.

Figure 4:
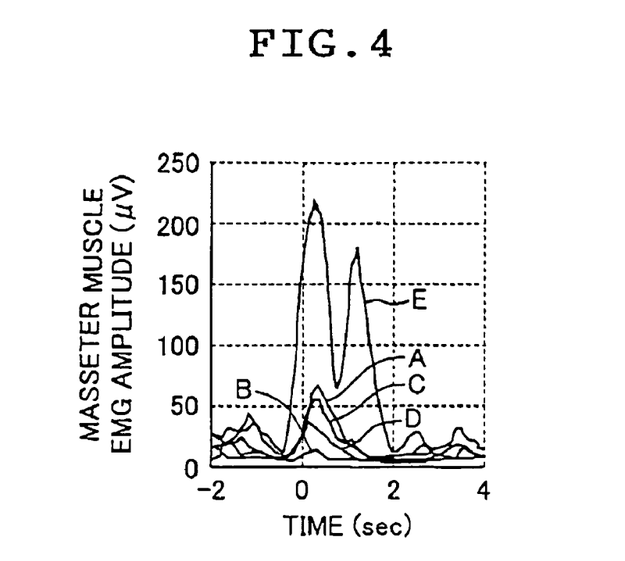
FIG. 4 is a graph showing myoelectric potential signals versus time.

FIG. 4 is a graph showing myoelectric potential signals versus time. In this example, myoelectric potential signals were obtained under different conditions on a per unit-time basis. In the graph, fluctuations in the myoelectric potential signals are appearing in the waveforms thereof. The waveforms A, B, C, D, and E show myoelectric potential signals during the work activities A, B, C, D, and E under different conditions. Among them, the waveform E has a sharp change. The sharp change can be judged by using the myoelectric potential signal parameter calculation module 32 mentioned above. A sharp change as in the waveform E shows the emergence of stress and the stress judgment module 35 judges the stress.

Figure 5:
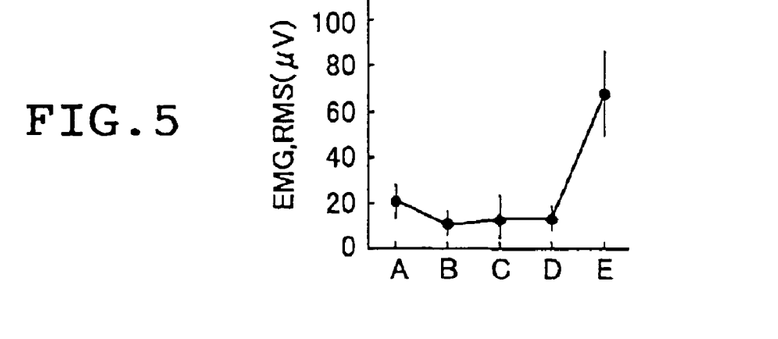
FIG. 5 is a graph showing the intensities of the myoelectric potential signals versus work activities.

FIG. 5 is a graph showing the intensities of the myoelectric potential signals versus the work activities, wherein A, B, C, D, and E show the individual work activities shown in FIG. 4. For the intensities of the myoelectric potential signals, the RMS is used herein. In this graph, the work activity E has an intensity higher than that of each of the other work activities. In the relationship represented by such a graph, the intensity calculation module 33 mentioned above calculates the RMS for each of the work activities, while the stress judgment module 35 compares individual values with each other and judges that larger stress is placed on a test subject in the case of the work activity E.

Next, as a comparative example, samples of the value subjective judgment values of the test target will be shown.

Figure 6:
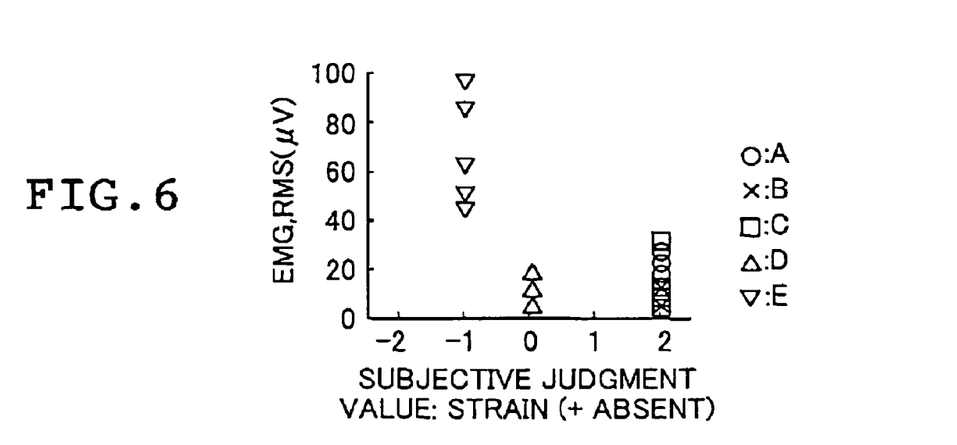
FIG. 6 is a distribution chart showing the myoelectric potential signals versus a subjective judgment value (strain)

FIG. 6 is a distribution chart showing the myoelectric potential signals versus a functional value (strain), wherein O denotes the work activity A, × denotes the work activity B, □ denotes the work activity C, Δ denotes the work activity D, and ∇ denotes the work activity E. Note that, the distribution chart shows samples of five test subjects. The absence of strain is represented by a positive value. During the work activity E denoted by ∇, in particular, all of the test subjects answered that strain had developed. The fact coincides with the result that the work activity E places large stress on each of the test subjects shown in FIGS. 4 and 5.

Figure 7:
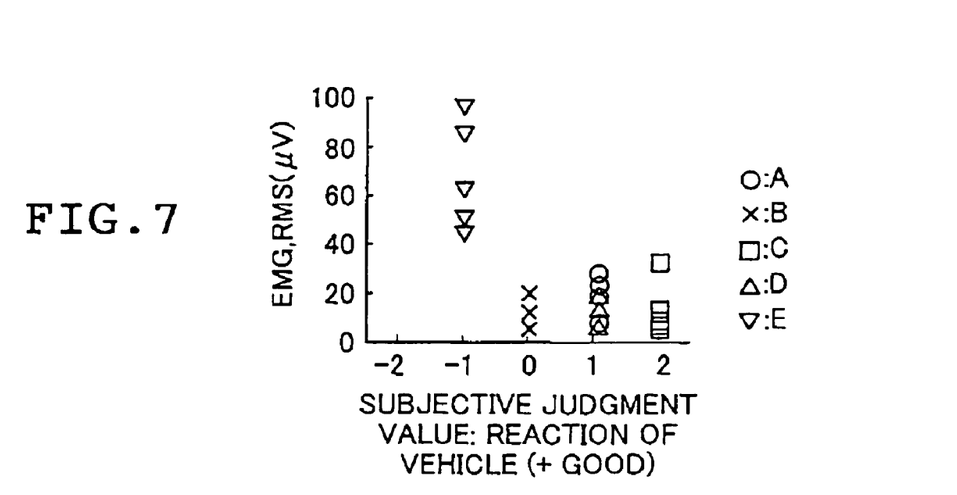
FIG. 7 is a distribution chart showing the myoelectric potential signals versus a subjective judgment value (reaction).

FIG. 7 is a distribution chart showing the myoelectric potential signals versus a subjective judgment value (reaction), wherein O denotes the work activity A, × denotes the work activity B, □ denotes the work activity C, Δ denotes the work activity D, and ∇ denotes the work activity E. In the case shown herein, each of the work activities has been imparted with a specified condition. Note that, the distribution chart shows samples of five test subjects. An excellent vehicle reaction is represented by a positive value. During the work activity E denoted by ∇, in particular, all of the test subjects answered that the reaction of the vehicle was poor. This indicates that each of the test subjects feels large stress shown in FIGS. 4 and 5 when the reaction of the vehicle is poor.

INDUSTRY APPLICABILITY

As described above, according to the present invention, the judgment of the stress undergone by the test subject while he or she is working on the activity can be performed through the recognition of a change in an at-work myoelectric potential signal. As a result, it becomes possible to quantitatively represent an item appearing as a mental burden on the test subject while he or she is steering a wheel as a driver (during a work activity) and objectively judge the stress during the steering of the wheel (during the work activity).

The invention claimed is:

1. A stress-at work judging apparatus comprising:
   myoelectric potential signal input means for receiving a myoelectric potential signal from a masseter muscle of a test subject during a target work activity, the target work activity performed by exercise of muscles in an arm or leg of the test subject, not by exercise of jaws of the test subject;
   stress judging means for judging stress of the test subject during the target work activity from an intensity or time-varying change of the myoelectric potential signal inputted through the myoelectric potential signal input means, wherein the stress judging means excludes from a target period for stress judgment a period of work activity comprising opening and closing the jaws; and
a display for displaying a result from the stress judging means,
wherein the stress judging means specifies the period of work activity during which the test subject is opening and closing the jaws by recognizing voice data acquired by recording a speech of the test subject.

2. The stress-at-work judging apparatus according to claim 1, wherein the target work activity is a vehicle steering operation performed by the test subject.

3. A stress-at-work judging computer program product encoded on a computer-readable medium for causing a computer to perform stress-at-work judgment, the computer program product comprising:
an input instruction for receiving a myoelectric potential signal from a masseter muscle of a test subject during a target work activity, the target work activity performed by exercise of muscles in an arm or leg of the test subject, not by exercise of jaws of the test subject, the myoelectric potential signal being inputted through a myoelectric potential signal input means;
a judgment instruction for judging stress of the test subject during the target work activity from an intensity or time-varying change of the myoelectric potential signal inputted through the myoelectric potential signal input means,
wherein the judgment instruction excludes from a target period for stress judgment a period of work activity comprising opening and closing the jaws; and
a display instruction for displaying a result of stress judgment,
wherein the judgment instruction specifies the period during which the test subject is opening and closing the jaws by recognizing voice data acquired by recording a speech of the test subject.

4. The stress-at-work judging program product according to claim 3, wherein the target work activity is a vehicle steering operation performed by the test subject.

5. A stress-at-work judging method comprising:
a myoelectric potential signal input step of receiving a myoelectric potential signal from a masseter muscle of a test subject during a target work activity, the target work activity performed by exercise of muscles in an arm or leg of the test subject, not by exercise of jaws of the test subject, the myoelectric potential signal being inputted through a myoelectric potential signal input means;
a stress judging step for judging stress of the test subject during the target work activity from an intensity or time-varying change of the myoelectric potential signal inputted through the myoelectric potential signal input means,
wherein the stress judging step excludes from a target period for stress judgment a period of work activity comprising opening and closing the jaws; and
a display step of displaying a result of the stress judgment step,
wherein the stress judging step specifies the period of work activity during which the test subject is opening and closing the jaws by recognizing voice data acquired by recording a speech of the test subject.

6. The stress-at-work judging method according to claim 5, wherein the target work activity is a vehicle steering operation performed by the test subject.

7. A stress-at-work judging apparatus comprising:
myoelectric potential signal input means for receiving a myoelectric potential signal from a masseter muscle of a test subject during a target work activity, the target work activity performed by exercise of muscles in an arm or leg of the test subject, not by exercise of jaws of the test subject;
stress judging means for judging stress of the test subject during the target work activity from an intensity or time-varying change of the myoelectric potential signal inputted through the myoelectric potential signal input means,
wherein the stress judging means excludes from a target period for stress judgment a period of work activity comprising opening and closing the jaws; and
a display for displaying a result from the stress judging means,
wherein the stress judging means specifies the period of work activity during which the test subject is opening and closing the jaws, by visually recognizing video data acquired by video recording a face of the test subject.

8. A stress-at-work judging computer program product encoded on a computer-readable medium for causing a computer to perform stress-at-work judgment, the computer program product comprising:
an input instruction for receiving a myoelectric potential signal from a masseter muscle of a test subject during a target work activity, the target work activity performed by exercise of the muscles in an arm or leg of the test subject, not by exercise of the jaws of the test subject, the myoelectric potential signal being inputted through a myoelectric potential signal input means;
a judgment instruction for judging stress of the test subject during the target work activity from an intensity or time-varying change of the myoelectric potential signal inputted through the myoelectric potential signal input means,
wherein the judgment instruction excludes from a target period for stress judgment a period of work activity comprising opening and closing the jaws; and
a display instruction for displaying a result of stress judgment,
wherein the judgment instruction specifies the period of work activity during which the test subject is opening and closing the jaws, by visually recognizing video data acquired by video recording a face of the test subject.

9. A stress-at-work judging method comprising:
a myoelectric potential signal input step of receiving a myoelectric potential signal from a masseter muscle of a test subject during a target work activity, the target work activity performed by exercise of muscles in an arm or leg of the test subject, not by exercise of jaws of the test subject, the myoelectric potential signal being inputted through a myoelectric potential signal input means;
a stress judging step for judging stress of the test subject during the target work activity from an intensity or time-varying change of the myoelectric potential signal inputted through the myoelectric potential signal input means,
wherein the stress judging step excludes from a target period for stress judgment a period of work activity comprising opening and closing the jaws; and
a display step of displaying a result of the stress judgment step,
wherein the stress judging step specifies the period of work activity during which the test subject is opening and closing the jaws, by visually recognizing video data acquired by video recording a face of the test subject.

* * * * *

UNITED STATES PATENT AND TRADEMARK OFFICE
CERTIFICATE OF CORRECTION

PATENT NO.         : 7,421,293 B2                                                   Page 1 of 1
APPLICATION NO.    : 10/522022
DATED              : September 2, 2008
INVENTOR(S)        : Kuramori et al.

It is certified that error appears in the above-identified patent and that said Letters Patent is hereby corrected as shown below:

On the Title Page, Item (75) (Inventors), Line 9, please change "Yoshjo" to --Yoshio--.

On the Title Page, Item (57) (Abstract), Line 34, please change "An" to --A--.

In Column 1, Line 4, please add the following:

FOREIGN PRIORITY DATA

Priority is claimed on Japanese Patent Application No. 2002-212683, filed July 22, 2002, and is a National Phase of PCT Application No. JP03/09160, filed July 18, 2003.

In Column 8, Line 65, please change "or" to --of--.

In Column 10, Line 60, please change "nodule" to --module--.

Signed and Sealed this

Fourteenth Day of April, 2009

JOHN DOLL
*Acting Director of the United States Patent and Trademark Office*